United States Patent [19]

Perry, Jr.

[11] 4,396,019

[45] Aug. 2, 1983

[54] VAGINAL MYOGRAPH METHOD AND APPARATUS

[76] Inventor: John D. Perry, Jr., 50 Lawn Ave., Portland, Me. 04102

[21] Appl. No.: 271,532

[22] Filed: Jun. 8, 1981

Related U.S. Application Data

[63] Continuation-in-part of Ser. No. 47,635, Jun. 11, 1979, abandoned, and a continuation-in-part of Ser. No. 883,872, Mar. 6, 1978, abandoned.

[51] Int. Cl.$^3$ .............................................. A61B 5/05
[52] U.S. Cl. .................................... 128/733; 128/778
[58] Field of Search ........................ 128/733, 778, 642

[56] References Cited

U.S. PATENT DOCUMENTS

| | | | |
|---|---|---|---|
| 3,620,208 | 11/1971 | Higley | 128/639 |
| 3,640,284 | 2/1972 | De Langis | 128/778 X |
| 3,898,983 | 8/1975 | Elam | 128/778 X |
| 3,905,355 | 9/1975 | Brudny | 128/733 X |
| 3,920,003 | 11/1975 | Ash et al. | 128/734 X |
| 3,924,609 | 12/1975 | Friedenberg et al. | 128/738 |
| 3,933,147 | 1/1976 | Du Vall et al. | 128/778 X |
| 3,995,492 | 12/1976 | Clyhes | 73/379 |
| 4,033,332 | 7/1977 | Hardway, Jr. et al. | 128/774 X |
| 4,080,961 | 3/1978 | Eaton | 128/642 |

OTHER PUBLICATIONS

Perritt, R. Q. et al., "A Simple Inexpensive 8-Channel Multiplexer for Electromyography in Human Locomotion", MBE, Jan. 1976 pp. 104–106.

*Primary Examiner*—Kyle L. Howell
*Assistant Examiner*—Francis J. Jaworski
*Attorney, Agent, or Firm*—Eliot S. Gerber

[57] ABSTRACT

Apparatus and method for the measurement of and assistance in the treatment of the pubococcygeus muscle of the human using myographic biofeedback. A single probe with a plurality of separated noble metal smooth-faced sensing electrodes detects minute electrical pulses in the range of zero to twenty-five microvolts (RMS). The impulses are transmitted through connecting cables to electronic circuits which amplify the impulses and transform them into visual, auditory, or tactile signals which are presented to the patient, as a biofeedback signal, in real time. The apparatus and method is used to diagnose, train and exercise the pubococcygeus muscle under conscious control, and is useful in the treatment of several pathological conditions of the female pelvic organs, including sexual inadequacy, and in research concerning human sexual response.

3 Claims, 10 Drawing Figures

VAGINAL MYOGRAPH METHOD AND APPARATUS

DETAILED DESCRIPTION OF THE INVENTION

The present invention is a continuation-in-part application based upon an application entitled "Vaginal Myograph", Ser. No. 883,872, filed Mar. 6, 1978, now abandoned, and Ser. No. 047,635 (Design) filed June 11, 1979, now abandoned.

The present invention relates to apparatus and methods for the measurement of and assistance in the treatment of chronic or acute weakness or atrophy of the pubococcygeus muscle group in the human.

In humans the pubococcygeus muscle group provides major anatomic support for three important pelvic structures: the urethra, the vagina, and the rectum. Atonic or inadequate functioning of the pubococcygeus muscle has been associated with a variety of medical and psychological problems, ranging from hernial protrusions and urinary stress incontinence to sexual frigidity or inadequacy. Recent medical concern for female sexual dysfunction has focused on therapy of this muscle as the main physiological treatment.

Prior to the present invention, there were two very different therapeutic approaches to the treatment of dysfunction of the pubococcygeus muscle group. The most widely used therapy was based on the voluntary regime developed by Dr. Arnold Kegel of the University of California. The common descriptions of this approach explain that the appropriate exercise involves repeatedly cutting off the outflow of urine. Unfortunately, this therapy is not always effective in practice and often results in wasted or misdirected muscular effort. Moreover, the patients who have the most severe conditions are the least able to carry out the exercise properly.

An alternative to the voluntary exercise approach of Dr. Kegel has been one or another form of direct electrotherapy of the pubococcygeus muscle group. A number of patents have suggested that probes inserted into the vagina and having electrical conductors may be used to force contractions of the pubococcygeus muscle. In the DeLangis U.S. Pat. No. 3,640,284 entitled "Apparatus for Electrotherapy of the Pubococcygeus" electric pulses in the range 20 Hz to 8 K Hz with low and high currents are applied through a probe. The DeLangis U.S. Pat. No. 3,640,284, in addition to its probe having two ring electrodes 11,12 for injecting electrical pulses, also shows a water-filled bladder connected to a manometer pressure gauge for measuring muscle activity. Similarly, in the DuVall U.S. Pat. No. 3,933,147 entitled "Apparatus and Method For Treating Disorders in the Region of the Pubococcygeus Muscle" a probe injects electrical pulses having a frequency of 200 Hz and up to 10 volts for a period of about one second each. A probe for electrical stimulation of the anal sphincter muscles is shown in German Offenlegungsschrift No. 2502164; British Pat. No. 1,145,749 entitled "Muscle Stimulators"; and U.S. Pat. No. 3,749,100 entitled "Suppository Electrode Structure".

The DeLangis and DuVall devices, and other electrical signal injecting devices, suffer from common problems which have limited their use. They require the application of an electrical shock to the human body which, however mild in intent, necessitates close supervision of the manufacture, design and application of the devices. In addition, such electrical shocks are strongly feared and objected to by many patients. Another objection to electrotherapy of the vagina is that it attempts to teach voluntary control by means of involuntary stimulation. The patient is essentially passive during the treatment while, according to current theory, it is precisely that passivity which has resulted in the pathological condition in the first place.

The article entitled "A Fetal Electrocardiographic Electrode" by Edward H. Hon, printed in *The Yale Journal of Biology and Medicine*, Volume 39, August 1966, describes a clamp electrode which is attached to the scalp of the fetus to obtain signals "in the range of 300 to 500 microvolts". The electrode, as shown in FIGS. 1A and 1B, is a silver-silver chloride positive electrode which has pins to attach the electrode to the scalp of the fetus. The leads are negative and positive to measure D.C. and are connected to a conventional EEG (electrocardiograph) circuit to record the heartbeat of the fetus. A similar device is shown in U.S. Pat. No. 4,080,961 to Eaton entitled "Fetal Scalp Electrode Instrument". In U.S. Pat. No. 4,080,961 a fetus scalp electrode is attached to the head of the fetus using a grasping electrode 22 having clamp pins 33,32. The electrode leads, as in the Hon article, may be connected to an EKG device for detecting the heartbeat of the fetus. Since the electrodes in the Hon and Eaton devices penetrate the skin of the fetus, they would only be used in a hospital operating room or other suitable medical facility.

A number of prior art patents show the use of a pneumatic device to measure muscle activity. Such devices generally comprise a resilient tube, for example, of rubber, which is filled with air. When the tube is compressed by the muscle activity, the rise in air pressure is measured by a gauge. For example, U.S. Pat. No. 4,048,985 entitled "Exercise Device" shows an elongated flexible closed tube filled with air or other fluid and connected to a pressure indicating gauge. The U.S. Pat. No. 4,048,985 implies that the device may be used to test and strengthen the vaginal musculature.

Similarly, in U.S. Pat. No. 3,683,893 entitled "Muscle Activity Recorder" a resilient collapsible bellows 11 filled with air is connected to an electrical pressure indicating device through a series of mechanical linkages. The electrical device includes a potentiometer as one arm of a bridge circuit. The patent states that the bellows may be used as a feedback system (myotonal-kinesthetic feedback system) for use with the training of vaginal musculature.

A pressure sensitive bladder is also shown in U.S. Pat. No. 3,898,983 entitled "Device and Method For Detecting The Degree of Muscle Relaxation of a Medical Patient", in which the clenching or flexing of fingers is detected by gas pressure in the flexible bladder, the pressure changes being detected by a gas pressure gauge or a strain gauge.

It has also been suggested that the intensity of pelvic muscle activity, and specifically the pubococcygeus muscle, may be measured by a strain gauge. In DuVall's U.S. Pat. No. 3,933,147 entitled "Apparatus and Method for Treating Disorders in the Region of the Pubococcygeus Muscle", mentioned above, the same probe that is used to involve involuntary contractions may also measure voluntary or involuntary contractions. The probe includes a stainless steel band 0.002 inch thick connected to a strain gauge heaving leads connected to a meter (column 6, line 6–column 7, line 17). A strain gauge is also utilized in U.S. Pat. No. 3,474,776 entitled "Intrauterine Muscle Activity Measuring System", in which a flexible cantilever-beam is moved by muscle activity such as uterine muscle activity to provide an electrical output of a strain gauge positioned as an arm of a bridge circuit.

It has also been suggested that electrical current, from an outside source, may be conducted by the skin or body of a patient to detect heart action or other body functions. In U.S. Pat. No. 3,620,208 entitled "EKG Amplifying Electrode Pickup" the maximum permissible current is one microamp. The U.S. Pat. No. 3,620,208 shows a pick-up (transducer) for an electrocardiograph (EKG) in which a stainless steel sensor plate (column 2, lines 20–22) has a bias current of −10 nanoamps (column 2, line 52).

It has also been suggested that battery action may be utilized in a probe. A silver rectal pessary having rings of gold metal for a galvanic battery action is shown in British Pat. No. 230,967 entitled "Improvements in Rectal Pessaries" and a similar device having rings of dissimilar metals, for battery action, is shown in U.S. Pat. No. 1,042,624 entitled "Rectal Dynamo".

The use of bio-feedback as a procedure to train muscle activity is well-known. For example, U.S. Pat. No. 3,905,355 entitled "System For The Measurement, Display and Instrumental Conditioning of Electromyographic Signals" shows an EMG (electromyograph) using a set of electrodes connected to a central computer and display, the electrodes not being described in detail. An audible feedback signal is produced by the exercise device of U.S. Pat. No. 3,995,492 entitled "Sound Producing Isometric Exerciser."

In U.S. Pat. No. 4,033,332, a contactless monitor for breathing regularity, a patient lies on a variable capacitance pad.

Other patents show detection of direct current potential of the body, especially to detect ovulation. In U.S. Pat. No. 3,920,003 to Ash entitled "Detecting Small Potential Differences In A Mammalian Body" two body contacts are described and the detection of the potential (electrical) difference taken across the two contacts, i.e., a type of GSR-Galvanic Skin Response. One contact is a probe, which is of "base metals" (column 2, line 5) having conductive sections of "carbon impregnated polymer" such as conductive rubber (column 2, line 34) to detect vaginal contact potential. The other contact, which is on a different part of the body separated from the first contact, may be the handle of the probe, a conductive body sucker, a belt or a hand contact. The direct current (potential difference) (column 6, line 19) is said to be normally 10–15 millivolts but 0 or negative upon ovulation (column 1, lines 66–68).

Similarly, in U.S. Pat. No. 3,924,609 to Friedenberg entitled "Detector Device and Process For Detecting Ovulation" the "low D.C. potentials of the order of milli-volts" (Abstract) are detected using two electrodes, for example, two hand contacts (column 2, lines 18–20). Friedenberg, like Ash, is a type of GSR-Galvanic Skin Response (skin potential response) system which measures DC voltage taken across two spaced-apart electrodes, one of which is on the skin.

OBJECTIVES AND FEATURES OF THE INVENTION

It is an objective of the present invention to provide an electromyograph probe to detect and measure the variable electrical activity, in the range of 0–25 microvolts at 100–400 Hertz a.c., associated with contraction of the pubococcygeus muscle and to indicate such measurements for biofeedback training.

It is a further objective of the present invention to provide such a probe and a measuring system matched thereto, so that a skin contact electrode is not needed, the probe itself being the only electrode carrier.

It is a further objective of the present invention to provide such a probe which is sufficiently sensitive to such electrical activity so that a contact lubricant is not required.

It is a further objective of the present invention to provide such a probe which will provide an absolute measurement of muscle tension uninfluenced by relative physical size and which distinguishes a tensioned muscle (which may be voluntary and unaware or involuntary and unaware) from a non-tensional muscle at rest. In contrast, fluid-filled bladders or strain gauges are influenced by the size of the opening relative to the measuring device and are comparison instruments which are "zeroed" to provide a baseline measurement at rest; such baseline measurement being unable to distinguish between tensioned muscles and muscles at rest.

It is a further objective of the present invention to provide such a probe which does not inject any electrical signals to the user's body, thereby eliminating the possibility of electrical shock or other electrically induced adverse side effects.

It is a further objective of the present invention to provide such a probe which is constructed of materials which do not react with body fluids or tissues.

It is a further objective of the present invention to provide such a probe which is designed to be retained in the correct location, after positioning, and without the necessity of external clamping means.

Another objective of the present invention is to provide a theraputic device which may be both inexpensive and portable, and may therefore be employed by the patient in the privacy and convenience of the home, with only periodic professional supervision.

Another objective of the present invention is to provide a means of measuring minute responses of a sexual nature for purposes of pure research into the normal mechanisms of human sexuality, including responses which may not be strong enough to be apparent at either the conscious level nor at a level which could be measured by existing devices.

SUMMARY OF THE INVENTION

In accordance with the present invention, apparatus is provided which senses, directly through the vaginal or rectal tissue, the minute impulses of activity of the pubococcygeus muscle. These impulses, resulting from willful nerve activity on the part of the patient, are picked up by electrodes on a probe and transmitted to appropriate electronic amplifiers having a gain in the order of 1,000,000. These amplified signals are processed by various logic circuits to derive various forms of display, including visual, auditory and tacile, in both analog and digital form. In accord with documented studies of the principles of biofeedback, immediate knowledge of the results leads to "learning" of conscious and willful control over the muscle's tension. Myographic biofeedback has been widely employed in the treatment of stress-related illnesses (the theraputic intent is a reduction of muscular tension) and in muscular rehabilitation therapies (the therapeutic intent is increased muscular activity). The vaginal myograph of the present invention indicates the voluntary activity of the neuromuscular control system (nerves and brain); unlike devices which only electrically excite the pubococcygeus muscle for their involuntary reaction. The invention of the vaginal myograph makes it possible to apply the science of biofeedback to the treatment of sexual inadequacy.

BRIEF DESCRIPTION OF THE DRAWINGS

Further objectives of this invention, as well as the novel features thereof, will become apparent when one studies the following description of the embodiments of the invention, taken in conjunction with the accompanying figures, in which.

DETAILED DESCRIPTION OF THE INVENTION

Figure 1:
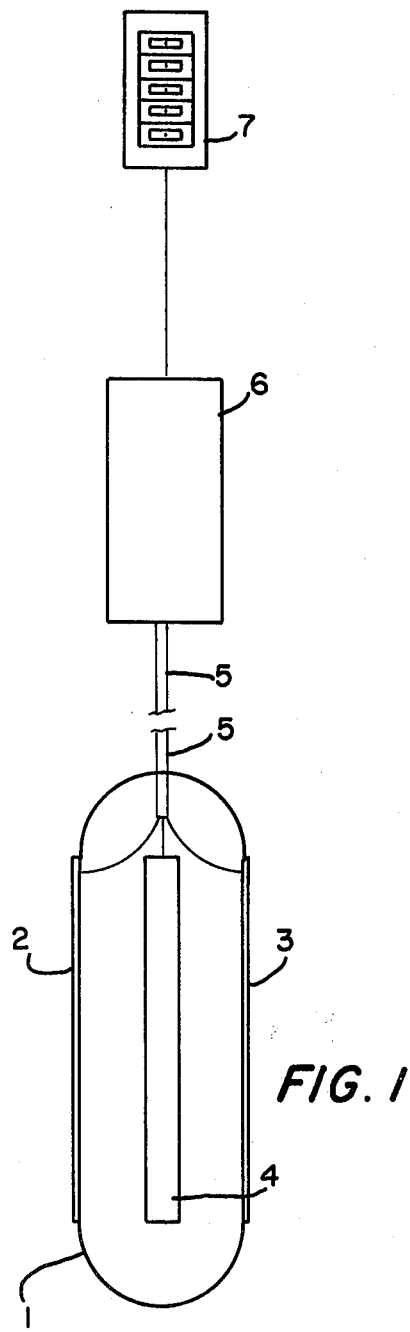
FIG. 1 shows the Vaginal Myograph as a cylindrical probe supporting three electrodes and an output cable which connects them to the electronic circuitry.

In FIG. 1 is shown the first embodiment of the Vaginal Myograph probe of the present invention. In general, the probe consists of a cylinder 1 of about 1 inch o.d., made of inert plastic resin electrically non-conductive material, which supports two active electrodes 2,3 and a neutral or ground electrode 4. The electrodes are of a noble metal, preferably silver, and have an elongated longitudinal smooth surface so that they may have appropriate contact with the vaginal walls. Surprisingly, it has been found that the natural liquid secretions of the vaginal walls are sufficiently conductive so that a conductive lubricant need not be applied to the probe. The same cylinder also serves to anchor a shielded connecting table 5, which connects to the electronic circuits 6 which process the signals and present the biofeedback display 7. The cylinder 1 is filled with a suitable sealing material, such as pourable acrylic resin, to make it watertight and sterilizable, as well as to provide mechanical strength.

Figure 2:
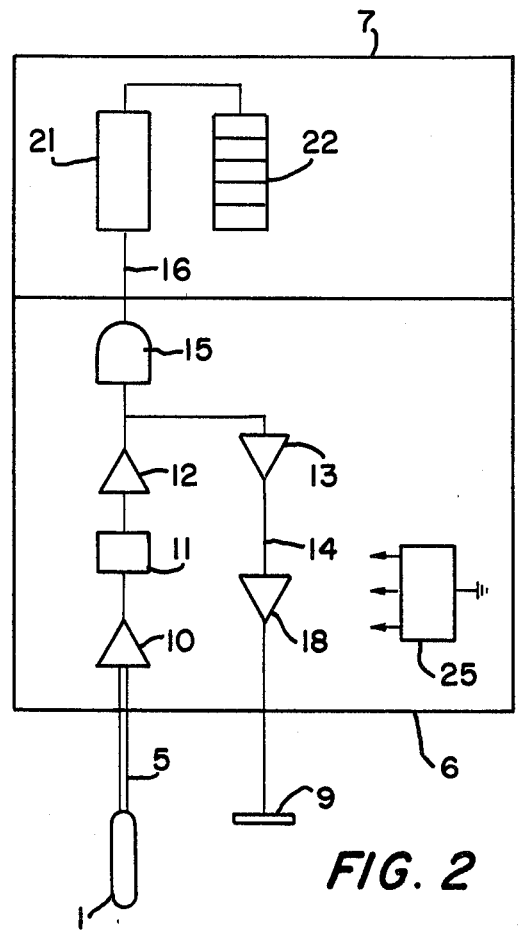
FIG. 2 shows in block form the electronic and logic circuits capable of amplifying and transforming the input signals into useful biofeedback displays of signals.

The preferred electronic circuits for signal detection and processing are shown in FIG. 2. Electrical signals traveling to the nerves which serve the pubococcygeus muscle are detected through the vaginal wall, i.e., on the side of the vaginal wall, by the active electrodes 2,3 transmitted through the cable 5 to the differential inputs of an operational amplifier pre-amplifier which includes a FET (field effect transistor) input stage. Those electrical signals are detected by at least two separated electrodes in reference to a third electrode and are in the range of 0 to 25 microvolts (root mean square-RMS), the peak-to-peak voltages being higher. The detected signals are shaped by a 100–1000 Hz Bandpass filter 11 and the main amplifier 12 which may consist of one or more stages. An analog output is available at 14, buffered by a unity-gain voltage follower 13. A schmidt trigger 15 provides binary output 16 to the biofeedback display 7.

The preferred biofeedback display utilizes a voltage controlled oscillator 18 which drives an output device 9 which may be either a loudspeaker (for auditory feedback) or transducer (for tactile feedback). In general, the voltage controlled oscillator is set to produce no sound on zero input, and increasing pitch proportional to the increase in nerve impulses, representing increased tension in the pubococcygeus muscle. Controls (not shown) may be provided to set the range and threshold of the VCO.

An alternative biofeedback display consists of a frequency counter 21 which drives a L.E.D. (Light Emitting Diode) "Seven Segment" (number) display 22. The display shows the number of nerve impulses received at the electrode site during the previous one-second interval, and is refreshed every one second. Adjustment of the offset bias of the main amplifier 12 controls the threshold signal level for activation of the schmidt trigger and hence determines the minimum signal level to be counted.

Figure 3:
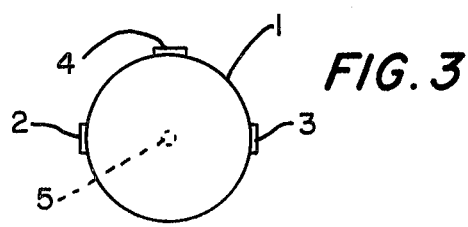
FIG. 3 shows a frontal view of the cylindrical probe.

FIG. 3 shows the cylindrical probe from the front.

Figure 4:
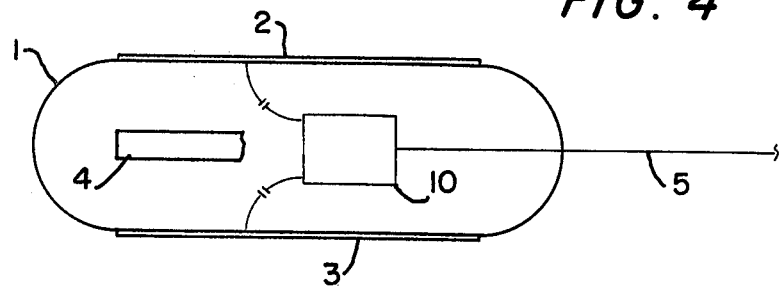
FIG. 4 shows a variation of the Vaginal Myograph probe, wherein a pre-amplifier is incorporated directly into the probe body, for use in electrically "noisy" environments.

FIG. 4 shows the Vaginal Myograph probe of the present invention with an integrated circuit pre-amplifier 10 installed and sealed within the cylinder of the probe. This modification results in improved signal-to-noise ratio, and may find application in portable "take-home" versions of the invention where electrical interference might be objectionable.

Figure 5:
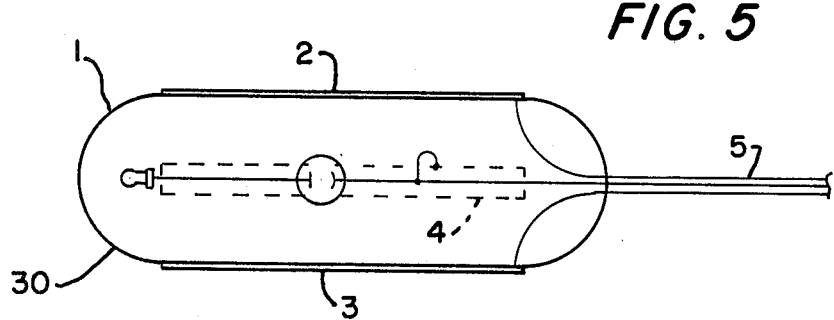
FIG. 5 shows the Vaginal Myograph incorporated into a probe containing a Vaginal Photoplethsmograph.

As shown in FIG. 5, the Vaginal Myograph may be incorporated into the same probe assembly as a vaginal photoplethysmograph 30. The Vaginal Photoplethysmograph, developed by Geer and Sintchak at the State University of New York at Stony Brook, measures vaginal blood changes by means of changes in the amount of light striking the photocell due to varying blood levels present in the tissues, and is a good indicator of Master's and Johnson's First (Excitement) and Fourth (Resolution) Stages of Sexual Arousal. The Vaginal Myograph measures their Second (Plateau) and Third (Orgasm) Stages; together they are capable of assessing the full range of female sexual response.

Figure 6:
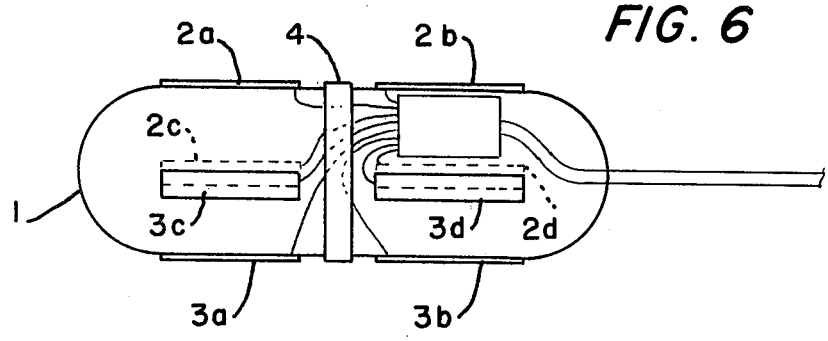
FIG. 6 shows an expanded version of the Vaginal Myograph, containing eight pairs of active electrodes and multiplexing circuits to select electrode combinations.
Figure 7:
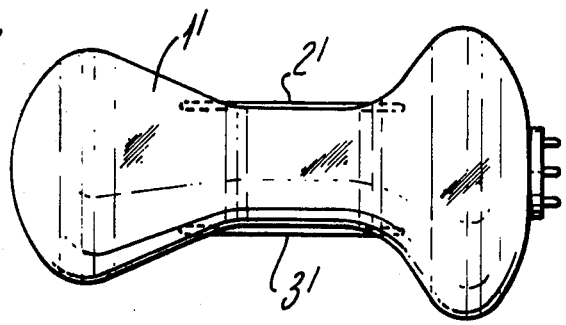
FIG. 7 shows a top view of a second embodiment of the probe of the present invention.
Figure 8:
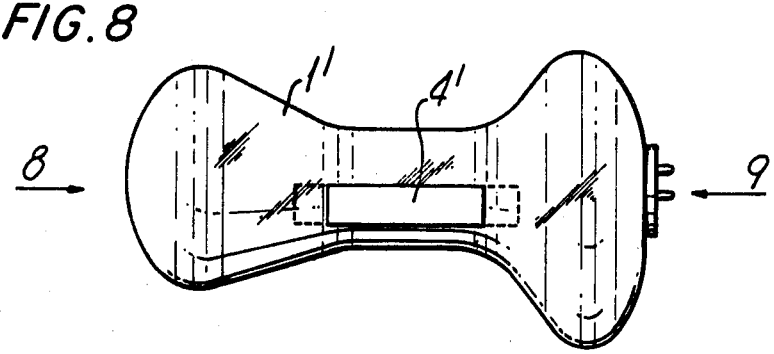
FIG. 8 shows a side elevational view of the probe of FIG. 7.
Figure 9:
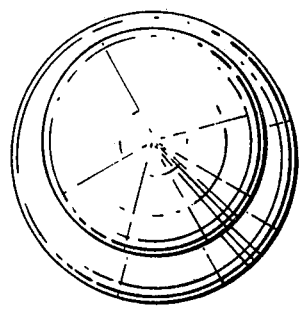
FIG. 9 is an end view taken along lines 9—9 of FIG. 8.
Figure 10:
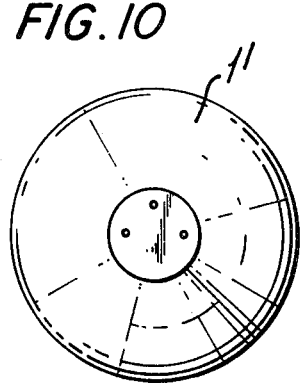
FIG. 10 is an end view taken along lines 10—10 of FIG. 8.

FIG. 6 shows an expanded version of the Vaginal Myograph. Four pairs of active electrodes are provided (however, the device may be adapted to fewer or more pairs as necessary); the integrated circuit multiplexer under control of external logic circuits selects pairs of electrodes in sequence for transmission of electronic impulses over a connecting cable to measure different sections of the tissue. This version may find use in research applications.

In the probe shown in FIGS. 7–10, the preferred embodiment of the present invention, the probe body 1' of plastic resin is saddle-shaped as seen from the side. It is a right-sided cylinder, round in cross-section, and with a wide "U" shape in side view. This shape has been found by experimentation to locate the electrodes 2', 3' and 4' in the best location for detecting the minute electrical signals. The electrodes 2', 3' (active) and 4' (ground) are smooth-faced silver electrodes elongated in the longitudinal direction, i.e., parallel to the imaginary central axis which is perpendicular to line 10–10. The electrodes 2'–4' are embedded in the body 1' but their conductive faces are exposed and are part of the surface of the probe. The terminals 5' are connectable to a cable and detect the electrical activity in the zero to 25 microvolt range and in the alternating current 100–400 Hz. frequency range. The circuitry of FIG. 2 may be used with any of the probes of the present invention. Although its filter is 100–1000 Hz. bandwidth, it has been found satisfactory for the 100–400 Hz. signal.

Accordingly, while I have described my invention in connection with a specific embodiment thereof, it is clearly to be understood that this is done only by way of example and not as a limitation to the scope of my invention as set forth in the objectives thereof and in the claims.

What is claimed is:

1. Apparatus for the physiological monitoring of the pubococcygeus muscle of the patient-subject through the vaginal or rectal wall of said patient-subject comprising:

an electromyography probe for contacting the wall of the vagina or rectum of a patient-subject;

said probe including an electrically non-conductive body and at least three electrically conductive electrodes constituting part of the surface of the probe body, one of the said electrodes being a reference electrode, the electrodes being formed of precious metal and each electrode being electrically insulated from the other electrode of the probe, said electrodes detecting electromotive signals at least at three places of said wall, said signals ranging in voltage from zero to twenty-five microvolts and being an alternating frequency in the range of 100–400 Hz., said signals being emitted when the pubococcygeus muscle of the patient-subject is exercised pursuant to a willful attempt of the patient-subject to exercise said muscle; said electrodes being contact electrodes which are smooth on their external contact surface so as to contact the wall without injury and without externally applied contact lubricant;

said probe carried electrodes being the only active body contact electrodes of the apparatus and said electrodes not injecting electrical signals to the said wall; and transducer means coupled to said electrodes for amplifying and transforming said electromotive signals into sensory signals which are sensed by the patient-subject for biofeedback development of the pubococcygeus muscle.

2. Apparatus according to claim 1 wherein said transducer means includes amplifier means within said probe.

3. The method of biofeedback physiological monitoring and training of the pubococcygeus muscle of the patient-subject comprising:

inserting an electromyography probe into contact with the wall of the vagina or rectum of a patient-subject, said probe not being lubricated with electrical contact lubricant;

said probe including an electrically non-conductive body and at least three electrically conductive electrodes constituting part of the external face of the probe body, the electrodes being formed of precious metal and each electrode electrically insulated from the other electrode of the probe; said electrodes being contact electrodes which are smooth on their external contact surface so as to contact the wall without injury and without externally applied contact lubricant;

using said electrodes to detect electromotive signals at least at three places of said wall, said signals ranging in voltage from zero to twenty-five microvolts and at an alternating current frequency of 100–400 Hz.; said signals being emitted when the pubococcygeus muscle of the patient-subject is exercised pursuant to a willful attempt of the patient-subject to exercise said muscle;

said probe carried electrodes being the only active body contact electrodes of the apparatus and said electrodes not injecting electrical signals to the said wall; and amplifying and transforming said electromotive signals into sensory signals using transducer means coupled to said electrodes, said transducer means filtering out electrical noise outside of the said voltage and frequency means, the sensory signals being sensed by the patient-subject for biofeedback development of the pubococcygeus muscle.

* * * * *